United States Patent [19]

Le Roy

[11] 4,077,399

[45] Mar. 7, 1978

[54] CRANIAL TRANSILLUMINATION DEVICE

[75] Inventor: Pierre L. Le Roy, Wilmington, Del.

[73] Assignee: New Research and Development Laboratories, Inc., Wilmington, Del.

[21] Appl. No.: 710,930

[22] Filed: Aug. 3, 1976

[51] Int. Cl.² .............................................. A61B 1/06
[52] U.S. Cl. ..................................... 128/23; 128/2 L
[58] Field of Search ........... 128/23, 395, 2 L, 2.05 P, 128/2.05 T, 41, 76 R

[56] References Cited

U.S. PATENT DOCUMENTS

| | | | |
|---|---|---|---|
| 792,162 | 6/1905 | Potter | 128/41 |
| 2,442,462 | 6/1948 | Kirchbaum | 128/2 L |
| 3,227,155 | 1/1966 | Erickson | 128/2 L |
| 3,527,932 | 9/1970 | Thomas | 128/2 L |
| 3,628,525 | 12/1971 | Polanyi et al. | 128/2 L |
| 3,648,685 | 3/1972 | Hepp et al. | 128/2 L |
| 3,699,955 | 10/1972 | Heath | 128/76 R |

*Primary Examiner*—Robert W. Michell
*Assistant Examiner*—Henry S. Layton
*Attorney, Agent, or Firm*—Connolly and Hutz

[57] ABSTRACT

Cranial transillumination device includes a shielded light source mounted in a cup-like housing and connected by an intermediate band to a similarly shielded light meter for indicating any abnormal spiral fluid accumulation on the brain.

7 Claims, 2 Drawing Figures

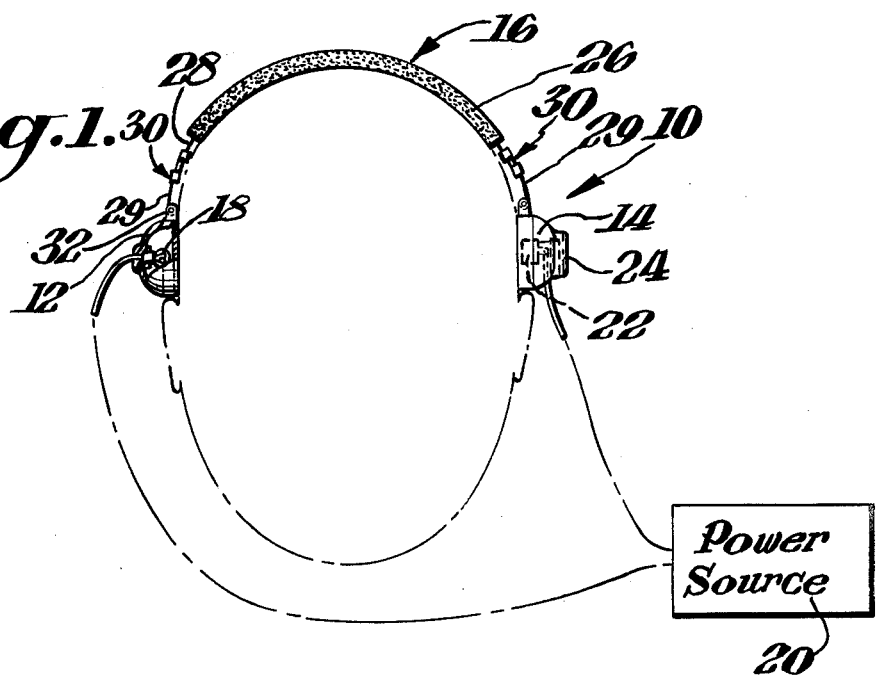
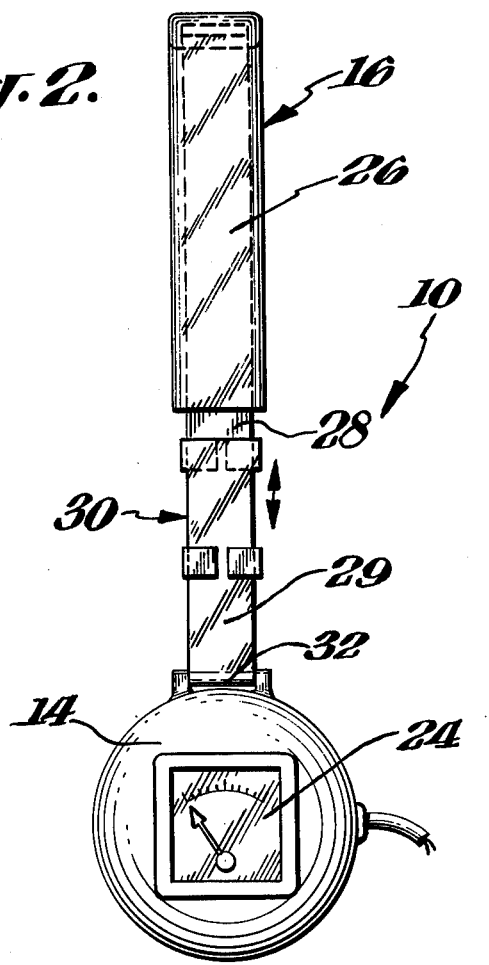

CRANIAL TRANSILLUMINATION DEVICE

BACKGROUND OF THE INVENTION

This invention relates to a transillumination device and more particularly to a cranial transillumination device for determining whether or not there is any abnormal spinal fluid accumulation on the brain. Such procedures are generally done on children. The most common practice is similar to egg candling where the child is placed in a relatively dark room and a source of light is disposed on one side of the child's head. The passage of light through the head would be evident in the dark room to indicate such an abnormal spinal fluid accumulation. This procedure has the obvious disadvantage of frightening the child because of the necessity for a dark room.

U.S. Pat. No. 3,527,932 discloses a transilluminating arrangement which utilizes a conventional flashlight provided with a cylindrical hood or shield for being pressed against the head of the child. Although the patent indicates that the arrangement obviates the need for the room being completely dark, such an arrangement should not effectively indicate the transmission of light through the head without some degree of darkening of the room.

SUMMARY OF THE INVENTION

An object of this invention is to provide a cranial transillumination device which may be used in a normally lit room without requiring any special darkening.

A further object of this invention is to provide such a cranial transillumination device which effectively indicates the presence of abnormal spinal accumulation with a quantitative meaningful indication.

In accordance with this invention the cranial transillumination device includes a shielded light source mounted in a conformable cup-like housing and connected by an intermediate band to a similarly shielded light meter for indicating any abnormal fluid accumulation on the brain.

The light indicating means may be a conventional photocell to which an externally visible light meter is electrically connected. The headband may be adjustable to permit its adaptability to various size children and may include pivotal attachments for the cups containing the light source and light meter to assure a firm fitting of the cups to the head.

THE DRAWINGS

FIG. 1 is a front elevation view partly in section showing the cranial transillumination device of this invention; and FIG. 2 is a side elevation view of the device of FIG. 1.

DETAILED DESCRIPTION

FIG. 1 illustrates the cranial transillumination device 10 of this invention. As indicated therein the first cup 12 is connected to a second cup 14 by means of an intermediate band 16. Each cup is open at one end but otherwise light impervious. Cup 12 houses a suitable light source 18 suitably powered by any convenient conventional power source 20. Cup 14 in turn houses light sensitive means which in the schematically illustrated form is a photocell 22 having connected thereto a light meter 24 (FIG. 2) with the same power source 20 being utilized therefor. Headband 16 may be of any suitable construction which preferably provides adjustability for the device for rendering it adaptable for use with different patients. In the illustrated form headband 16 includes a padded central sleeve 26 into which is inserted a metal plate-like member 28. Each cup 12, 14 has attached thereto a metal plate-like member 29 which is arranged for sliding contact on top of central plate 28. Suitable temporary locking devices 30 are provided to maintain the proper relationship of member 28, 29 so that the headband 16 may be adjusted for conforming to a particular patient and then locked in place. Although FIG. 1 illustrates band 16 in general contact with the head, the band may be spaced therefrom. Similarly, the band may be disposed about the back instead of the top of the head. As also illustrated each cup 12, 14 is pivotally connected to its respective plate 29 by shaft 32. Cups 12, 14 are made of a suitable flexible resilient cushioning material which may closely conform to the patient's head without causing undue discomfort. In this manner each cup 12, 14 provides a closed housing wherein its open end is closed by the patient's head.

In use power source 20 is actuated to illuminate light source 18. Any light transmitted through the head is detected by light detector or photocell 22 which is disposed generally in line with light source 18. Light meter 24 is connected to detector 22 and visually indicates a quantity reflecting the amount of light transmitted during the actual use of the device. Thus by virtue of the completely shielded light source and light detector and by virtue of the visible light meter it is possible to use the device in a normally lit room. Further the device 10 obviates the need to be hand held since it is mounted directly on the head.

What is claimed is:

1. A cranial transillumination device comprising a first housing, said first housing being open at one end and otherwise light impervious, a light source mounted in said first housing, a second housing, said second housing being open at one end and otherwise light impervious, a light sensor mounted in said second housing, mounting means in the form of a headband connecting said first and second housings with said open ends disposed toward each other, said headband being shaped to attach on the patient's head with said light source and said light sensor juxtaposed the patient's head in line with each other so that light may pass through the patient's head from said light source to reach and be detected by said sensor, and said first and second housings being made of a material capable of fitting snugly against the head of the patient to close said open ends whereby light emitted from said light source would be detected by said light sensor for indicating any abnormal spinal fluid accumulation.

2. The device of claim 1 wherein said first and second housings are cup shaped.

3. The device of claim 1 including a light meter responsive to said light detector for providing a visual indication of the amount of light transmitted through the head, and said light meter being externally visible from said second housing.

4. The device of claim 3 wherein said first and second housings are cup shaped.

5. The device of claim 4 wherein said headband is generally U-shaped and adjustable.

6. The device of claim 5 including common power means for said light source and said light sensor and said light meter.

7. The device of claim 6 wherein said open ends of said housings are disposed for being aligned with each other.

* * * * *